United States Patent [19]

De La Poterie et al.

[11] Patent Number: 6,010,686

[45] Date of Patent: *Jan. 4, 2000

[54] COSMETIC COMPOSITION INCLUDING A POLYMERIC SYSTEM, PREPARATION OF AND USE OF THIS COMPOSITION

[75] Inventors: Valérie De La Poterie, Le Chatelet En Brie; Isabelle Bara, Paris, both of France

[73] Assignee: L'Oreal, Paris, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/811,170

[22] Filed: Mar. 4, 1997

[30] Foreign Application Priority Data

Mar. 4, 1996 [FR] France ................................ 96 02682

[51] Int. Cl.[7] ............................. A61K 7/02; A61K 7/031; A61K 7/032

[52] U.S. Cl. ............................... 424/64; 424/63; 424/401; 514/844

[58] Field of Search ....................... 424/401, 63, 64, 424/70.7; 514/844

[56] References Cited

U.S. PATENT DOCUMENTS

| | | |
|---|---|---|
| 3,639,572 | 2/1972 | Heinrich et al. . |
| 4,336,246 | 6/1982 | Leon-Pekarek ......................... 424/70.6 |
| 4,383,539 | 5/1983 | Collins et al. ........................... 132/333 |
| 4,423,031 | 12/1983 | Murui et al. . |
| 4,574,082 | 3/1986 | Tietjen et al. .............................. 424/63 |
| 4,795,631 | 1/1989 | Sheehan . |
| 5,238,678 | 8/1993 | Shiozawa et al. . |
| 5,505,937 | 4/1996 | Castrogiovanni et al. ............... 424/64 |
| 5,534,247 | 7/1996 | Franjac et al. .......................... 424/70.7 |
| 5,538,717 | 7/1996 | Poterie ..................................... 424/61 |
| 5,601,808 | 2/1997 | Mellul et al. ............................. 424/61 |
| 5,725,845 | 3/1998 | Krog et al. ............................... 424/64 |
| 5,725,882 | 3/1998 | Kumar et al. .......................... 424/486 |
| 5,837,223 | 11/1998 | Barone et al. ............................ 424/64 |
| 5,843,417 | 12/1998 | Hanna et al. ......................... 424/70.7 |
| 5,849,275 | 12/1998 | Calello et al. ............................ 424/64 |
| 5,879,667 | 3/1999 | Hanna et al. ......................... 424/70.7 |
| 5,879,668 | 3/1999 | Hanna et al. ......................... 424/70.7 |
| 5,911,974 | 6/1999 | Brieva et al. ............................. 424/64 |

FOREIGN PATENT DOCUMENTS

| | | |
|---|---|---|
| 265228 | 4/1988 | European Pat. Off. . |
| 655234 | 5/1995 | European Pat. Off. . |
| 2229393 | 12/1974 | France . |
| 2679769 | 2/1993 | France . |
| WO92/19215 | 11/1992 | WIPO . |

OTHER PUBLICATIONS

Patent Abstract of Japan, vol. 16, No. 552 (c–1006) Nov. 20, 1992.

English Derwent Abstract of European Application No. EP 655234.

English Derwent Abstract of French Application No. FR 2229393.

*Primary Examiner*—Robert H. Harrison
*Attorney, Agent, or Firm*—Finnegan, Henderson, Farabow, Garrett & Dunner, L.L.P.

[57] ABSTRACT

A cosmetic composition for application to the skin, the semimucosae and/or the mucosae, including a polymeric system which includes an aqueous dispersion of particles of film-forming polymer, wherein the polymeric system makes it possible to obtain a supple and flexible film.

37 Claims, No Drawings

COSMETIC COMPOSITION INCLUDING A POLYMERIC SYSTEM, PREPARATION OF AND USE OF THIS COMPOSITION

The present invention relates to a composition, in particular, a cosmetic composition, capable of being applied to the skin, the semimucosae and/or the mucosae. The composition includes, in particular, an aqueous dispersion of particles of film-forming polymer and can be employed as a make-up or treatment product.

Compositions to be applied to the skin and/or the mucosae, of the lip rouge or foundation type are generally in the form of a stick, a flexible paste or a cast paste. Such compositions generally include fatty substances such as oils, pasty compounds and/or waxes and a particulate phase generally containing fillers and pigments.

When applied to the skin, however, these compositions exhibit the disadvantage of transferring, i.e., the composition is deposited, at least partially, on a support with which it is brought into contact, such as, for example, a glass, a garment or the skin. The composition leaves a mark on the support when it is deposited. This results in the disadvantages of a mediocre persistence of the composition on the skin or the mucosae and the need to reapply the composition regularly.

Another disadvantage of the compositions of the prior art lies in the problem of migration. It has been found, in fact, that some compositions tend to propagate inside fine lines and/or wrinkles of the skin in the case of foundations, in the fine lines which surround the lips in the case of lip rouges, and in the folds of the eyelid in the case of eyeshadows. It has also been found, especially in the case of eyeshadows, that streaks appear in the make-up, which are generated by the movements of the eyelids. It has further been found that eyeliners can also run. All these phenomena produce an unpleasant aesthetic effect which the consumer, quite obviously, wishes to avoid.

So-called "transfer-free" make-up compositions, capable of overcoming the above-mentioned disadvantages, are known. These compositions are based on fatty substances generally including volatile oils, especially volatile silicone oils and/or volatile hydrocarbon oils. However, these compositions produce a very matte make-up.

The objective of the present invention is to provide a composition which makes it possible to obtain a film of very good cosmetic behavior, i.e., which does not transfer, does not stain a support with which it comes into contact, and does not migrate over time, while making it possible to obtain a make-up and/or a glossy film.

Thus, a subject of the invention is a composition capable of being applied to the skin, the semimucosae and/or the mucosae, which comprises a polymeric system including an aqueous dispersion of particles of at least one film-forming polymer, wherein the polymeric system is present in an amount which makes it possible to obtain a film which has a hardness of less than approximately 110.

Another subject of the invention is the use, for treating the skin, in particular for making-up, protecting, therapeutically and/or nontherapeutically treating the skin, the semimucosae and/or the mucosae, in particular the lips, of a composition comprising a polymeric system in an amount effective to obtain a film, wherein the polymeric system includes an aqueous dispersion of particles of at least one film-forming polymer and makes it possible to obtain a film which has a hardness of less than approximately 110.

Another subject of the invention is a method for preparing a cosmetic composition capable of being applied to the skin, the semimucosae and/or the mucosae, and especially a lip rouge composition, which method comprises the step of including in a cosmetic composition a polymeric system containing an aqueous dispersion of particles of at least one film-forming polymer, wherein the polymeric system is present in an amount effective to obtain a film which has a hardness of less than approximately 110.

It has been found that the composition according to the invention can be applied easily and spreads easily and uniformly on the skin, the semimucosae and the mucosae, in particular on the lips.

The composition according to the invention makes it possible to obtain a homogeneous film which has a light texture and remains comfortable to wear all day long. The film is not at all sticky, while being soft, supple, elastic and flexible on the skin; it follows the movements of the support on which it is applied without cracking and/or lifting off. It adheres completely to the lips. The composition according to the invention therefore is particularly advantageous as a composition for application to the lips, especially as lip rouge. The composition according to the invention also is particularly advantageous as a composition for application as an eyeliner.

Furthermore, the film obtained in accordance with the present invention can be very glossy or more or less matte, depending on the nature of the particular constituents of the composition. This results in a wider range of make-up products which can be made glossy or matte at will.

As described above, the composition according to the invention includes a polymeric system which contains at least one aqueous dispersion of particles of at least one film-forming polymer. Among the film-forming polymers that can be employed in accordance with the present invention are synthetic polymers of the polycondensate type or of the radical type, polymers of natural origin, and mixtures thereof.

Among the polycondensates, mention may preferably be made of anionic, cationic, nonionic or amphoteric polyurethanes, acrylic polyurethanes, polyvinyl pyrrolidone polyurethanes, polyester polyurethanes, polyether polyurethanes, polyureas and mixtures thereof.

The polyurethane may be, for example, a polyurethane copolymer, polyurea/urethane or polyurea, which is aliphatic, cycloaliphatic or aromatic, comprising, by itself or as a mixture:

at least one block originating from linear or branched aliphatic and/or cycloaliphatic and/or aromatic polyester;

at least one block originating from aliphatic and/or cycloaliphatic and/or aromatic polyether;

at least one silicone-containing block, substituted or unsubstituted, branched or unbranched, for example, polydimethylsiloxane or polymethylphenylsiloxane;

at least one block comprising fluorine-containing groups; and mixtures thereof.

The polyurethanes as defined by the invention may also be obtained from polyesters, branched or unbranched, or from alkyls comprising mobile hydrogens which are modified by reaction with a diisocyanate and a difunctional (for example dihydro-, diamino-, or hydroxyamino-) organic compound, additionally comprising either a carboxylic acid or carboxylate group or a sulphonic acid or sulphonate group, or a neutralizable tertiary amine group or a quaternary ammonium group.

Polyesters, polyesteramides, polyesters containing a fatty chain, polyamides and epoxy ester resins may also be mentioned.

The polyesters may be obtained, in a known manner, by polycondensation of aliphatic or aromatic diacids with aliphatic or aromatic diols or polyols. Succinic acid, glutaric acid, adipic acid, pimelic acid, suberic acid or sebacic acid may be employed as aliphatic diacids. Terephthalic acid or isophthalic acid, or a derivative such as phthalic anhydride, may be employed as aromatic diacids. Ethylene glycol, propylene glycol, diethylene glycol, neopentyl glycol, cyclohexanedimethanol and 4,4'-(1-methylpropylidene) bisphenol may be employed as aliphatic diols. Glycerol, pentaerythritol, sorbitol and trimethylolpropane may be employed as polyols.

The polyesteramides may be obtained in a similar manner to the polyesters, by polycondensation of diacids with diamines or aminoalcohols. Ethylenediamine, hexamethylenediamine and meta- or para-phenylenediamine may be employed as diamine. Monoethanolamine may be employed as an aminoalcohol.

As a monomer carrying an anionic group capable of being employed during the polycondensation, mention may be made, for example, of dimethylolpropionic acid, trimellitic acid or a derivative such as trimellitic anhydride, the sodium salt of 3-sulphopentanediol acid and the sodium salt of 5-sulpho-1,3-benzenedicarboxylic acid.

Polyesters containing a fatty chain can be obtained by the use of diols containing a fatty chain during the polycondensation.

Epoxy ester resins can be obtained by polycondensation of fatty acids with a condensate containing $\alpha,\omega$-diepoxy ends.

Polymers of the radical type include acrylic and/or vinyl polymers or copolymers. Anionic radical polymers are preferably employed.

As a monomer carrying an anionic group capable of being employed during the radical polymerization mention may be made of acrylic acid, methacrylic acid, crotonic acid, maleic anhydride and 2-acrylamido-2-methylpropanesulphonic acid.

The acrylic polymers can result from the copolymerization of monomers selected from esters and/or amides of acrylic acid or of methacrylic acid. Examples of monomers of the ester type include methyl methacrylate, ethyl methacrylate, butyl methacrylate, isobutyl methacrylate, 2-ethylhexyl methacrylate and lauryl methacrylate. N-t-Butyl-acrylamide and N-t-octylacrylamide may be mentioned as examples of monomers of the amide type.

Preferred acrylic polymers include those obtained by copolymerization of monomers containing ethylenic unsaturation containing hydrophilic groups, preferably of nonionic nature such as hydroxyethyl acrylate, 2-hydroxypropyl acrylate, hydroxyethyl methacrylate and 2-hydroxypropyl methacrylate.

The vinyl polymers may result from the homopolymerization or copolymerization of monomers selected from vinyl esters, styrene or butadiene. Examples of vinyl esters which may be mentioned include vinyl acetate, vinyl neodecanoate, vinyl pivalate, vinyl benzoate and vinyl t-butylbenzoate.

It is also possible to employ acrylic/silicone copolymers or nitrocellulose/acrylic copolymers.

Polymers of natural origin, optionally modified, may be selected from shellac resin, gum sandarac, dammars, elemis, copals, cellulose derivatives and mixtures thereof.

Mention may also be made of the polymers resulting from the radical polymerization of one or more radical monomers inside and/or partially at the surface of preexisting particles of at least one polymer selected from the group including polyurethanes, polyureas, polyesters, polyesteramides and/or alkyds. These polymers are generally called hybrid polymers.

The aqueous dispersion including one or more film-forming polymers can easily be prepared by a person skilled in the art on the basis of his or her general knowledge.

In order to improve the film-forming nature of a polymer, for example by lowering its glass transition temperature, a coalescing agent, which may be selected from known coalescing agents, may be added to the dispersion.

In the present description "dispersion of film-forming polymer" is intended to mean a dispersion capable of forming a film, including or not including a coalescing agent.

The solids content of the aqueous dispersions according to the present invention may range from 5 to 60% by weight, and preferably range from 30 to 40% by weight.

The composition of the invention may include from 1 to 60% by weight, preferably from 5 to 40% by weight, of dry solids of film-forming polymers.

The particle size of the polymers in aqueous dispersion may range from 10 to 500 nm and preferably ranges from 20 to 150 nm, which makes it possible to obtain a film which has a remarkable gloss.

In order to carry out the present invention, the polymeric system must therefore make it possible to obtain a film on the support onto which it, or a composition containing it, is deposited; the film needing to have a hardness of less than approximately 110. The film preferably has a hardness of less than 70 and more preferably of less than 55.

Furthermore, in a preferred embodiment, the polymeric system is selected so as to make it possible to obtain a film which has an elongation greater than approximately 200%, and, still more preferably, greater than 300%. Methods of measurement of elongation and of hardness are described below, before the examples.

In order to obtain the desired hardness and, optionally, elongation, it is possible to employ a compound capable of affecting these characteristics, namely a plasticizing agent.

The polymeric system according to the invention then includes an aqueous dispersion of particles of at least one film-forming polymer and a plasticizing agent.

The plasticizing agent may be selected from among all the compounds known to a person skilled in the art as being capable of fulfilling the required function. This agent may be water-soluble or water-insoluble and may optionally be in the form of an aqueous dispersion.

Mention may be made of the usual plasticizers such as the following which may be present alone or as part of a mixture:

glycols and their derivatives, such as diethylene glycol ethyl ether, diethylene glycol methyl ether, diethylene glycol butyl ether or diethylene glycol hexyl ether, ethylene glycol ethyl ether, ethylene glycol butyl ether, and ethylene glycol hexyl ether;

glycerol esters;

propylene glycol derivatives, and in particular propylene glycol phenyl ether, propylene glycol diacetate, dipropylene glycol butyl ether, tripropylene glycol butyl ether, propylene glycol methyl ether, dipropylene glycol ethyl ether, tripropylene glycol methyl ether, diethylene glycol methyl ether, and propylene glycol butyl ether;

esters of acids, such as citrates, phthalates, adipates, carbonates, tartrates, phosphates and sebacates;

oxyethylenated derivatives such as oxyethylenated oils, especially vegetable oils such as castor oil, and silicone oils; and polymers which are water-soluble or in aqueous dispersion, which have a glass transition temperature of less than 25° C., preferably less than 15° C.

The quantity of plasticizing agent is selected by the person skilled in the art on the basis of his or her general knowledge, so as to obtain a polymeric system resulting in a film which has the desired mechanical properties, while preserving the cosmetically acceptable properties of the composition.

The composition may additionally include dyes and/or pigments which are conventionally employed in the field of cosmetics and of make-up. The pigments may be present in the composition in a proportion ranging from 0 to 20% by weight of the final composition, and preferably in a proportion ranging from 1 to 5%. The pigments may be white or colored, inorganic and/or organic. Among the inorganic pigments, mention may be made of titanium, zirconium or cerium dioxides and zinc, iron or chromium oxides and ferric blue. Among the organic pigments, mention may be made of carbon black and barium, strontium, calcium and aluminium lakes.

Any known additive may also be added to the composition according to the invention, such as thickening agents, for example clays, gums, silicas, cellulose derivatives, a synthetic polymer such as an acrylic polymer or an associative polymer of polyurethane type, a natural gum such as xanthan gum, spreading agents, dispersants, preservatives, antifoaming agents, wetting agents, UV filters, perfumes, fillers, cosmetic or pharmaceutical active agents, hydrating agents, vitamins and their derivatives and biological substances and their derivatives.

A person skilled in the art will, of course, take care to select this or these optional additives and/or their quantity in such a way that the advantageous properties of the composition according to the invention are not, or are not substantially, impaired by the envisaged addition.

The pH of the final composition obtained is preferably less than 9. This composition must, of course, be capable of being deposited on a support such as the skin or the mucosae.

The composition according to the invention may be in a fluid, gelled, semisolid, flexible paste or even solid form, such as a stick or rod.

The composition according to the invention finds application in particular as a product for make-up, especially as lip rouge, foundation, blusher, eyeshadow or eyeliner. An application may also be envisaged in the field of care compositions or treatment compositions, such as sun compositions, dermatological compositions or pharmaceutical compositions to be applied to the skin and/or the mucosae.

The invention is illustrated in greater detail in the following examples.

EXAMPLES (A) Measurement of Elongation

The elongation of the film obtained was measured according to the standard ASTM Standards, volume 06.01 D 2370-92 "Standard Test Method for Tensile Properties of Organic Coatings".

(B) Measurement of Hardness

The hardness of the film was measured according to standard ASTM D-43-66 or standard NF-T 30-016 (October 1981), with the aid of a PERSOZ pendulum.

The film deposited on the support was required to have a thickness of 300 microns before drying.

After drying for 24 hours at 30° C. and at a relative humidity of 50%, a film was obtained which had a thickness of approximately 100 microns; its hardness was then measured at 30° C. and 50% relative humidity.

Example 1

Aqueous dispersions including polymers which have various hardness values were prepared. The hardness of the film obtained was measured and the behavior of the film on the lips was assessed.

The following results were obtained:

| Polymer | Hardness | Visual assessment |
|---|---|---|
| Polyurethane 1 SANCURE 815 | 170 | cracks a little; lifts off after some time |
| Polyurethane 2 SANCURE 2060 | 165 | cracks very quickly in the middle of the lips; lifts off on the sides |
| Polyurethane 3 NEOREZ R-974 | 115 | cracked a little; lifts off after some time |
| Polyurethane 4 NEOREZ R-981 | 104 | long time to crack; did not lift off |
| Polyurethane 5 SANCURE 2255 | 45 | very long time to crack; did not lift off |
| Polyurethane 6 SANCURE 878 | 33.5 | very long time to crack; did not lift off |
| Polyurethane 7 SANCURE 861 | 24 | did not crack; very supple |

Example 2

An eyeliner was prepared which had the following composition:

| | |
|---|---|
| aqueous dispersion of polyurethane (SANCURE 861) | 95 g |
| pigment | 2 g |
| plasticizing agent (glycerine) | 1.25 g |

A composition was obtained which was easy to apply to the outline of the eye, which gave a satiny line and which did not transfer or run.

Example 3

A lip rouge was prepared which had the following composition:

| | |
|---|---|
| aqueous dispersion of polyurethane (NEOREZ R-981) | 95 g |
| pigment | 1 g |
| plasticizing agent (glycerine) | 1.25 g |

A composition was obtained which was easy to apply to the lips; the film obtained was glossy; it did not transfer or migrate into fine lines; it resisted well and followed the movement of the lips.

Example 4 (Comparative)

A lip rouge was prepared which had the following composition:

| | |
|---|---|
| aqueous dispersion of polyurethane (SANCURE 2060) | 95 g |
| pigment | 1 g |
| plasticizing agent (glycerine) | 1.25 g |

A film was obtained which cracked very rapidly after it was applied to the lips.

What is claimed is:

1. A cosmetic composition for the skin, the eyes or the lips, said composition comprising a polymeric system, said polymeric system comprising a dispersion of particles of at least one film-forming polymer in an aqueous medium, said polymeric system being present in an amount effective to obtain a continuous film upon application to the skin, the eyes or the lips and dehydration of said aqueous medium, wherein said continuous film has a hardness of less than approximately 110.

2. A composition according to claim 1, wherein said at least one film-forming polymer is an anionic polyurethane, a cationic polyurethane, a nonionic polyurethane, an amphoteric polyurethane, an acrylic polyurethane, a polyvinylpyrrolidone polyurethane, a polyester polyurethane, a polyether polyurethane, a polyurea, a polyester, a polyesteramide, polyamide, an epoxy ester resin, an acrylic polymer, a vinyl polymer, an acrylic/vinyl copolymer, an acrylic/silicone copolymer, a nitrocellulose/acrylic copolymer, a polymer of natural origin, a hybrid polymer or mixtures thereof, wherein said polymer of natural origin is optionally modified.

3. A composition according to claim 1, wherein said aqueous dispersion comprises a solids content ranging from 5 to 60% by weight.

4. A composition according to claim 3, wherein said aqueous dispersion comprises a solids content ranging from 30 to 40% by weight.

5. A composition according to claim 1, wherein said composition comprises from 1 to 60% by weight of dry solids of said at least one film-forming polymer.

6. A composition according to claim 5, wherein said composition comprises from 5 to 40% by weight of dry solids of said at least one film-forming polymer.

7. A composition according to claim 1, wherein said film-forming polymer particles have a particle size ranging from 10 to 500 nm.

8. A composition according to claim 7, wherein said film-forming polymer particles have a particle size ranging from 20 to 150 nm.

9. A composition according to claim 1, wherein said film has a hardness of less than 70.

10. A composition according to claim 9, wherein said film has a hardness of less than 55.

11. A composition according to claim 1, wherein said film has an elongation greater than approximately 200%.

12. A composition according to claim 11, wherein said elongation is greater than approximately 300%.

13. A composition according to claim 1, wherein said polymeric system further comprises a plasticizing agent.

14. A composition according to claim 13, wherein said plasticizing agent is a glycol, a glycol derivative selected from diethylene glycol ethyl ether, diethylene glycol methyl ether, diethylene glycol butyl ether or diethylene glycol hexyl ether, ethylene glycol ethyl ether, ethylene glycol butyl ether, and ethylene glycol hexyl ether, a glycerol ester, a propylene glycol derivative selected from propylene glycol phenyl ether, propylene glycol diacetate, dipropylene glycol butyl ether, tripropylene glycol butyl ether, propylene glycol methyl ester, dipropylene glycol ethyl ether, tripropylene glycol methyl ether, diethylene glycol methyl ether, and propylene glycol butyl ether, an ester of an acid, an oxyethylenated oil, a polymer which is water-soluble or in aqueous dispersion and which has a glass transition temperature of less than 25° C., or mixtures thereof.

15. A composition according to claim 14, wherein said esters of acids are citrates, phthalates, adipates, carbonates, tartrates, phosphates or sebacates.

16. A composition according to claim 14, wherein said oxyethylenated derivatives are vegetable oils and silicone oils.

17. A composition according to claim 14, wherein said polymers have a glass transition temperature of less than 15° C.

18. A composition according to claim 1, further comprising at least one dye or pigment.

19. A composition according to claim 18, wherein said at least one pigment is present in an amount greater than 0% and up to 20% by weight of the final composition.

20. A composition according to claim 18, wherein said at least one pigment is titanium, zirconium and cerium dioxides, zinc, iron and chromium oxides, ferric blue, carbon black and barium, strontium, calcium and aluminium lakes.

21. The composition according to claim 1, which is in the form of a skin and/or mucosae treatment composition, a dermatological composition, a sun composition, a pharmaceutical composition or a make-up product.

22. A composition according to claim 1, wherein said film does not transfer, migrate over time, or stain.

23. A composition according to claim 21, wherein said make-up product is a lip rouge, a foundation, a blusher, an eyeshadow or an eyeliner.

24. A composition according to claim 23, which is in the form of a lip rouge.

25. A composition according to claim 1, wherein said polymeric system is present in an amount effective to obtain a glossy film.

26. A method for preparing a cosmetic composition for the skin, the eyes or the lips, said method comprising the step of including in said composition a polymeric system in an amount effective to obtain a continuous film having a hardness of less than approximately 110, said polymeric system comprising a dispersion of particles of at least one film-forming polymer in an aqueous medium, wherein said polymeric system provides, upon application to the skin, the eyes or the lips and dehydration of said aqueous medium, said continuous film.

27. A method for cosmetically treating the skin, the eyes or the lips, said method comprising the step of applying to said skin, eyes or lips a cosmetic composition comprising a polymeric system, said polymeric system comprising a dispersion of particles of at least one film-forming polymer in an aqueous medium, said polymeric system being present in an amount effective to obtain a continuous film upon application to the skin, the eyes or the lips and dehydration of said aqueous medium, wherein said continuous film has a hardness of less than approximately 110.

28. A method according to claim 27, wherein said film does not transfer, migrate over time, or stain.

29. A method according to claim 27, wherein said film is supple, elastic, and/or flexible on said skin, eyes or lips.

30. A method according to claim 27, wherein said film follows the movements of said skin, eyes or lips, does not crack, and/or does not lift off said skin, eyes or lips.

31. A method according to claim 27, wherein said film is a glossy film.

32. A method according to claim 27, wherein said cosmetic treatment comprises protecting and/or nontherapeutically treating the sin, the eyes or the lips.

33. A method according to claim 27, wherein said cosmetic treatment comprises therapeutically treating the skin, the eyes or the lips.

34. A method according to claim 27, wherein said cosmetic treatment comprises making up the skin, the eyes or the lips.

35. A lip composition, said composition comprising a polymeric system comprising a dispersion of particles of at least one film-forming polymer in an aqueous medium, and said polymeric system being present in an amount effective to obtain a continuous film upon application to the lips and dehydration of said aqueous medium, wherein said continuous film has a hardness of less than approximately 110.

36. An eyeliner composition, said composition comprising a polymeric system comprising a dispersion of particles of at least one film-forming polymer in an aqueous medium, and said polymeric system being present in an amount effective to obtain a continuous film upon application to the skin around the eyes and dehydration of said aqueous medium, wherein said continuous film has a hardness of less than approximately 110.

37. A skin make-up composition, said composition comprising a polymeric system comprising a dispersion of particles of at least one film-forming polymer in an aqueous medium, and said polymeric system being present in an amount effective to obtain a continuous film upon application to the skin and dehydration of said aqueous medium, wherein said continuous film has a hardness of less than approximately 110.

\* \* \* \* \*